(12) United States Patent
Flanagan et al.

(10) Patent No.: US 8,703,168 B2
(45) Date of Patent: Apr. 22, 2014

(54) MEDICAL DEVICES FOR RELEASING THERAPEUTIC AGENT AND METHODS OF MAKING THE SAME

(75) Inventors: Aiden Flanagan, Galway (IE); Robert Herrmann, Boston, MA (US); Ken Merdan, Loretto, MN (US); Michael Kuehling, Munich (DE); Barry O'Brien, Galway (IE); Rajesh Radhakishnan, Bothell, WA (US); Torsten Scheuermann, Munich (DE); Scott Schewe, Eden Prairie, MN (US); Anurag Singhal, Ashland, MA (US); Young-Ho Song, Natick, MA (US); Mary Joe Timm, Littleton, MA (US); Jan Weber, Maastricht (NL); Yixin Xu, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1377 days.

(21) Appl. No.: 12/109,677

(22) Filed: Apr. 25, 2008

(65) Prior Publication Data
US 2009/0123517 A1    May 14, 2009

Related U.S. Application Data

(60) Provisional application No. 60/913,967, filed on Apr. 25, 2007, provisional application No. 60/977,835, filed on Oct. 5, 2007.

(51) Int. Cl.
*A61F 2/00*    (2006.01)

(52) U.S. Cl.
USPC .......................................... 424/423; 424/424

(58) Field of Classification Search
None
See application file for complete search history.

(56) References Cited

U.S. PATENT DOCUMENTS

| | | | |
|---|---|---|---|
| 5,824,048 A | 10/1998 | Tuch | |
| 5,866,204 A | 2/1999 | Robbie et al. | |
| 6,206,065 B1 | 3/2001 | Robbie et al. | |
| 6,491,666 B1 * | 12/2002 | Santini et al. | 604/191 |
| 6,709,379 B1 * | 3/2004 | Brandau et al. | 600/3 |
| 2002/0004101 A1 | 1/2002 | Ding et al. | |
| 2004/0106914 A1 * | 6/2004 | Coppeta et al. | 604/892.1 |
| 2005/0055014 A1 * | 3/2005 | Coppeta et al. | 604/890.1 |
| 2005/0060021 A1 * | 3/2005 | O'Brien et al. | 623/1.15 |
| 2005/0070989 A1 * | 3/2005 | Lye et al. | 623/1.4 |
| 2005/0129731 A1 | 6/2005 | Horres et al. | |
| 2005/0159805 A1 | 7/2005 | Weber et al. | |
| 2005/0186241 A1 * | 8/2005 | Boyle et al. | 424/423 |
| 2006/0195176 A1 | 8/2006 | Bates et al. | |
| 2007/0224235 A1 | 9/2007 | Tenney et al. | |

FOREIGN PATENT DOCUMENTS

WO    00/30610    6/2000

OTHER PUBLICATIONS

Robbie et al. Review of Scientific Instruments 2004 75:1089-1097.*
Thin Films and GLAD, Glancing Angle Deposition, An Overview of Thin Films and GLAD, http://www.ece.ualberta.ca/~glad/glad.html, 2006.
Communication Relating to the Results of the Partial International Search, PCT/US2008/061538, Jul. 9, 2008.
International Search Report and Written Opinion, PCT/US2008/061538, Sep. 22, 2008.

* cited by examiner

*Primary Examiner* — Robert A Wax
*Assistant Examiner* — Caralynne Helm
(74) *Attorney, Agent, or Firm* — Kenyon & Kenyon LLP

(57) ABSTRACT

An implantable medical device for releasing therapeutic agent having a medical device body and a plurality of reservoir-defining structures disposed on a surface of the body. A reservoir can be defined by the reservoir-defining structures and therapeutic agent may be located in the reservoir. A cover may extend over the reservoir so that the therapeutic agent is released from the reservoir when the medical device implanted. Methods for making the medical device may also include providing a medical device body, positioning a plurality of reservoir-defining structures on a surface of the body to form a reservoir, loading therapeutic agent into the reservoir, and covering the reservoir so that the therapeutic agent may release when the medical device is implanted. Alternatively, the reservoir may be covered with a cover and an opening formed in the cover so that the therapeutic agent may release when the medical device is implanted.

23 Claims, 12 Drawing Sheets

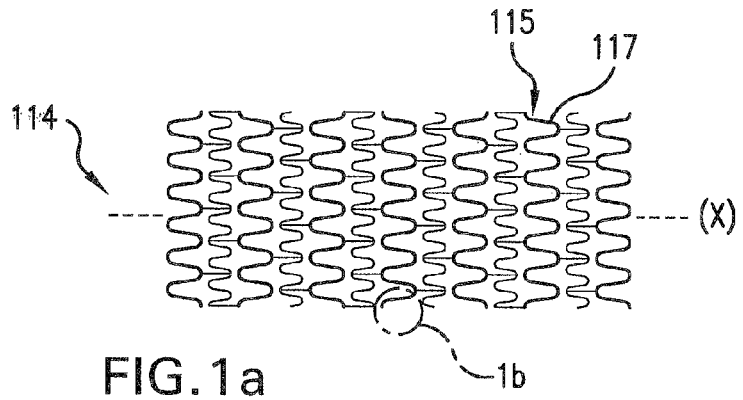
FIG.1a
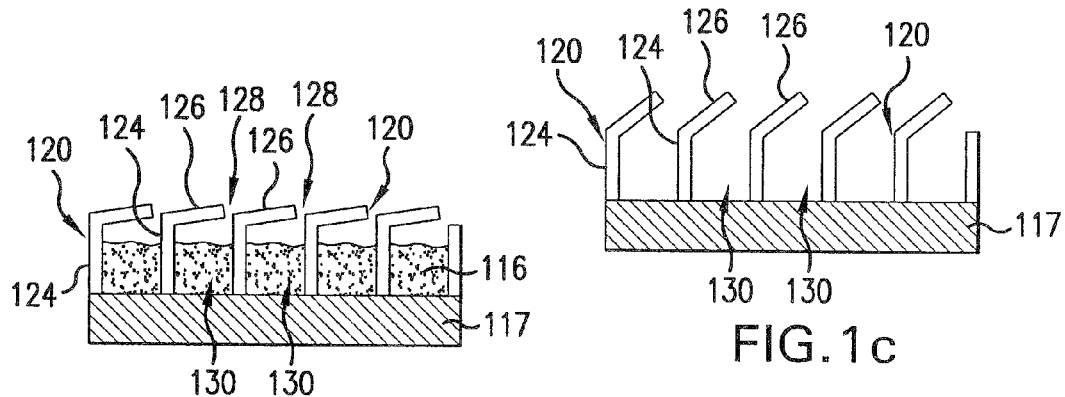
FIG.1b
FIG.1c
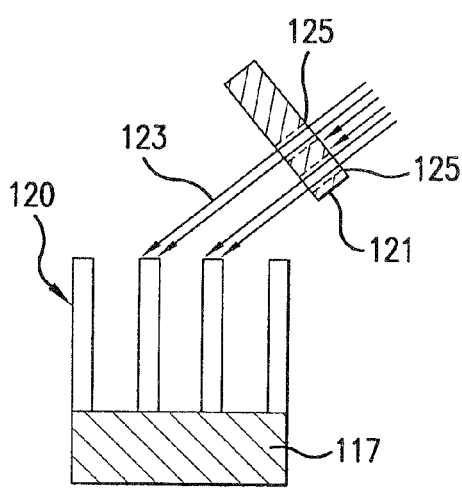
FIG.1d
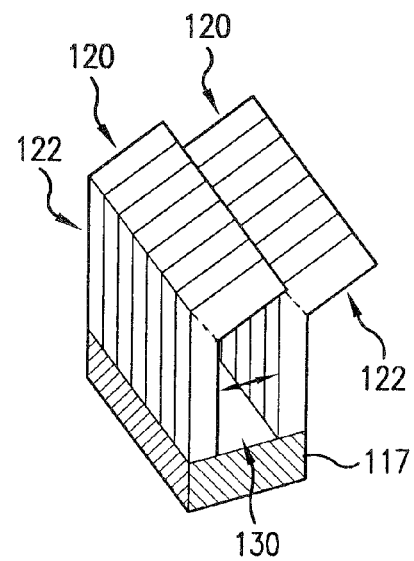
FIG.1e

Step 510
Providing a Medical Device Body

Step 520
Positioning a Plurality of Reservoir Defining Structures on a Surface of the Body to Form a Plurality of Reservoirs

Step 530
Loading Therapeutic Agent into the Reservoirs

Step 540
Covering the Reservoirs Almost Completely Such that an Opening Exists so that the Therapeutic Agent is Released When the Medical Device is Implanted

FIG.5

Step 710
Providing a Medical Device Body

Step 720
Positioning a Plurality of Reservoir Defining Structures on a Surface of the Body to Form a Plurality of Reservoirs

Step 730
Loading Therapeutic Agent into the Reservoirs

Step 740
Covering the Reservoirs With a Cover

Step 750
Forming an Opening in the Cover so that the Therapeutic Agent is Released Through the Opening when the Medical Device is Implanted

FIG. 7

Step 910
Providing a Medical Device Having Inner and Outer Surfaces.

Step 920
Forming a First Porous Layer Having a First Average Pore Size on at least one of the Inner and Outer Surfaces.

Step 930
Loading Therapeutic Agent into the First Porous Layer.

Step 940
Forming a Second Porous Layer with a Second Average Pore Size on Top of an Outer Surface of the First Porous Layer, Wherein the Second Average Pore Size is Less Than the First Average Pore Size.

FIG.9

Step 1110
Providing a Medical Device Having Inner and Outer Surfaces.

Step 1120
Applying a Series of Protrusions to at Least one of the Inner and Outer Surfaces.

Step 1130
Forming a First Porous Layer Having a First Average Pore Size on at least one of the Inner and Outer Surfaces Having the Protrusions.

Step 1140
Melting the Protrusions to Form Reservoirs Under the First Porous Layer.

Step 1150
Loading Therapeutic Agent into the Reservoirs Through the First Porous Layer.

Step 1160
Applying a Second Porous Layer with a Second Average Pore Size on Top of an Outer Surface of the First Porous Layer, Wherein the Second Average Pore Size may be Less than the First Average Pore Size.

FIG.11

Step 1310
Providing a Medical Device Having Inner and Outer Surfaces.

Step 1320
Forming a Reservoir Layer Comprised of a Plurality of Pores in or on at least One of the Inner and Outer Surfaces.

Step 1330
Loading the Pores with Therapeutic Agent.

Step 1340
Forming a Membrane Layer on Top of an Outer Surface of the Reservoir Layer.

FIG.13

MEDICAL DEVICES FOR RELEASING THERAPEUTIC AGENT AND METHODS OF MAKING THE SAME

CROSS REFERENCE TO RELATED APPLICATION

The present application claims priority to U.S. provisional application Ser. Nos. 60/913,967 filed Apr. 25, 2007 and 60/977,835 filed Oct. 5, 2007, the disclosures of which are incorporated herein by reference in their entirety.

TECHNICAL FIELD

The present invention generally relates to implantable medical devices and methods of making those devices.

BACKGROUND

The positioning and deployment of implantable medical devices within a target site of a patient are common, often repeated, procedures of contemporary medicine. These devices, which may be implantable stents, chronic rhythm management leads, neuromodulation devices, implants, grafts, defibrillators, filters, and catheters, as well as other devices, may be deployed for short or sustained periods of time and may be used for many medicinal purposes. These can include the reinforcement of recently re-enlarged lumens, the replacement of ruptured vessels, and the treatment of disease, such as vascular disease, through the delivery of therapeutic agent.

Coatings may be applied to the surfaces of implantable medical devices to transport therapeutic agent to a target site and to release it at the target site. In certain systems the therapeutic agent is released immediately upon reaching the target site. This burst release may not be favored in certain circumstances as a large amount of the therapeutic agent may be wasted as it is transported away by bodily fluids before it can be absorbed by the targeted area. Likewise, if large amounts of the therapeutic agent are released immediately upon deployment, less therapeutic agent will remain for sustained release of lower dosages over time.

BRIEF DESCRIPTION

The present invention is directed to implantable medical devices that are configured to release therapeutic agent to a target site of a patient and methods of making these implants. In embodiments of the present invention implantable medical devices may be configured to receive therapeutic agent and controllably release it over time when the implant is deployed at a target site. For example, implantable medical devices may include, but are not limited to, implantable stents, chronic rhythm management leads, neuromodulation devices, implants, grafts, defibrillators, filters, and catheters.

Embodiments of the present invention may include implantable medical devices having a medical device body and a plurality of reservoir-defining structures disposed on a surface of the body. A reservoir can be defined by the reservoir-defining structures and therapeutic agent may be located in the reservoir. A cover may extend over the reservoir so that the therapeutic agent may release from the reservoir when the medical device implanted.

Other embodiments of the present invention may include methods for making implantable medical devices which comprise the steps of providing a medical device body, positioning a plurality of reservoir-defining structures on a surface of the body to form at least one reservoir, loading therapeutic agent into the reservoir(s), and covering the reservoir(s) almost completely so that the therapeutic agent may release when the medical device is implanted.

Other embodiments of the present invention may include methods for making implantable medical devices which comprise the steps of providing a medical device body, positioning a plurality of reservoir-defining structures on a surface of the body to form at least one reservoir, loading therapeutic agent into the reservoir(s), and covering the reservoir(s) with a cover. An opening may be formed in the cover so that the therapeutic agent may release when the medical device is implanted.

Other embodiments of the present invention may include a method of making an implantable medical device for controllably releasing a therapeutic agent comprising the steps of providing a medical device having inner and outer surfaces, forming a first porous layer having a first average pore size on at least one of the inner and outer surfaces, loading therapeutic agent into the first porous layer, and forming a second layer on top of an outer surface of the first porous layer. The second coating layer may be a porous layer with a second average pore size less than the first average pore size.

Other embodiments of the present invention may include a method of making an implantable medical device for controllably releasing a therapeutic agent comprising the steps of providing a medical device having inner and outer surfaces, applying a series of protrusions to at least one of the inner and outer surfaces, forming a first porous layer having a first average pore size on the at least one of the inner and outer surfaces having the protrusions, melting the protrusions to form reservoirs under the first porous layer, loading therapeutic agent into the reservoirs through the first porous layer, and forming a second layer on top of an outer surface of the first porous layer. The second layer may be a porous layer with a second average pore size less than the first average pore size.

In accordance with yet still other embodiments, a method for making an implantable medical device for releasing a therapeutic agent may include providing a medical device having inner and outer surfaces, forming a reservoir layer comprised of a plurality of pores in or on at least one of the inner and outer surfaces, loading the plurality of pores with therapeutic agent, and forming a membrane layer on top of an outer surface of the reservoir layer to modulate and control the elution rate of the therapeutic agent in vivo. The plurality of pores in the reservoir layer may be formed, for example, by ion bombardment or by use of a laser. The membrane layer may be porous, with a smaller average pore size than the reservoir layer.

The invention may be embodied by numerous other devices and methods. The description provided herein, when taken in conjunction with the annexed drawings, discloses examples of the invention. Other embodiments, which incorporate some or all steps as taught herein, are also possible.

BRIEF DESCRIPTION OF THE DRAWINGS

Referring to the drawings, which form a part of this disclosure:

FIG. 1a shows a pattern of a stent;

FIG. 1b shows a cross-sectional view taken along line 1b-1b in FIG. 1a and showing reservoirs with therapeutic agent as may be employed in accordance with certain embodiments of the present invention;

FIG. 1c shows a cross-sectional view of a surface of an implantable medical device with a plurality of reservoir-defining structures including covers in an open position as may be employed in accordance with certain embodiments of the present invention;

FIG. 1d shows a guide member which may used in a GLAD process in accordance with certain embodiments of the present invention;

FIG. 1e shows an elevational view of two of the reservoir-defining structures of FIG. 1c;

FIG. 5 is a flow chart of method steps that may be employed in accordance with certain embodiments of the present invention;

FIG. 7 is a flow chart of method steps that may be employed in accordance with certain embodiments of the present invention;

FIG. 9 is a flow chart of method steps that may be employed in accordance with certain embodiments of the present invention;

FIG. 11 is a flow chart of method steps that may be employed in accordance with certain embodiments of the present invention;

FIG. 13 is a flow chart of method steps that may be employed in accordance with certain embodiments of the present invention.

DETAILED DESCRIPTION

Figure 2:
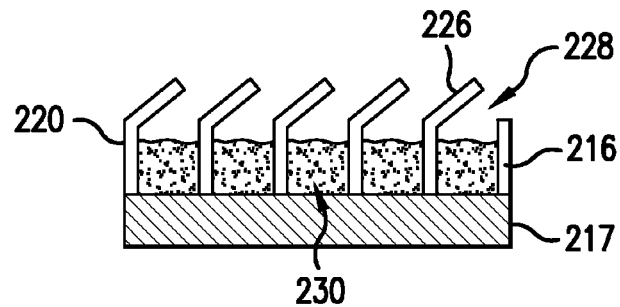
FIG. 2 shows a cross-sectional view of a surface of an implantable medical device with a plurality of reservoirs loaded with therapeutic agent as may be employed in accordance with certain embodiments of the present invention.

The present invention generally relates to implantable medical devices that deliver therapeutic agent to target sites of a body. This therapeutic agent may be carried such that it can be released by the implant for sustained periods of time at the target site. In embodiments of the present invention the therapeutic agent may be loaded into reservoirs that meter the release of the therapeutic agent. This metering may be accomplished through the use of small openings or passageways.

In some embodiments, the therapeutic agent may be transported, released or both without the use of additional carrier polymers. By reducing or eliminating the use of polymers the potential for inflammatory reactions associated with the use of polymers may be reduced or eliminated.

In still other embodiments, porous coatings having different pore sizes may be formed. For example, a reservoir layer comprised of pores having a first average pore size may be formed. The pores may then be loaded with therapeutic agent. Then, subsequent to loading of the pores with therapeutic agent, a membrane layer may be formed on an outer surface of the reservoir layer to modulate and/or control the elution rate of the therapeutic agent in vivo. The average pore size of the membrane layer may be less than the average pore size of the reservoir layer.

In still other embodiments, a reservoir layer may be formed directly in a surface of a medical device using, for example, ion processes (e.g., ion bombardment), grit blasting, chemical etching, or laser etching. The laser may utilize short duration pulses of radiation to melt a thin surface layer of the medical device to form a roughened surface. The roughened surface can have peaks and valleys. Formed between the peaks and valleys are a plurality of pores. The pores comprise a reservoir layer. The reservoir layer may be loaded with therapeutic agent and may be covered with a membrane layer, that may be porous, to control the release of the therapeutic agent in vivo. As an alternative to forming pores directly in a surface of the medical device, a layer of material may be coated onto the medical device and then pores formed in that layer.

Although in some embodiments a stent is shown, any implantable medical device may be used or made in accordance with embodiments of the present invention. For instance, implantable stents, cardiac rhythm management leads, neuromodulation devices, implants, grafts, defibrillators, filters, catheters and/or any implantable devices for systemic release of drugs may be used. The implantable medical devices may be self-expanding, mechanically expandable, or of a hybrid configuration which exhibits both self-expanding and mechanically expandable characteristics. The implantable medical devices may be made in a wide variety of designs and configurations, and may be made from a variety of materials including metals, ceramics, bio-ceramics, polymers, and/or combinations of these materials.

Referring initially to FIG. 1a, a stent 114 is shown which may facilitate the controllable release of a therapeutic agent. The stent 114 may comprise an elongate tubular body having a lattice portion 115 comprised of a plurality of struts 117. A plurality of reservoirs may be located on the struts 117.

As seen in FIGS. 1b-d, a plurality of reservoirs 130 may be formed in between reservoir-defining structures 120 located on the struts 117. Any suitable reservoir defining structures may be used, including, but not limited to, plates, posts, and columns. In the example shown, the reservoir-defining structures 120 may be comprised of a plurality of closely spaced or interconnected columns 122 (FIG. 1e). In FIG. 1e the columns 122 are closely spaced so that a row of columns 122 together form a divider. Two such dividers are shown in FIG. 1e.

Turning to FIG. 1b, therapeutic agent 116 may be stored in between these reservoir-defining structures 120. In the examples of FIGS. 1b and 1e, the reservoirs are channels formed in between adjacent rows of reservoir-defining structures 120; however, any suitable sizes and shapes may be used for the reservoirs. For instance, the reservoir-defining structures may be a plurality of posts or wires which form reservoirs, such as circular shaped reservoirs. The posts or wires may be formed of two different materials. For example, the head of the posts or wires may be formed of a softer material, that is easier to deform, than the body. In certain embodiments of the present invention, the head may be comprised of Ti and the body may be comprised of TiO2.

It should also be noted that the reservoir need not be completely bounded on all sides. For example, a reservoir may be an area surrounded by several posts or wires although there may be spaces between the posts or wires.

Covers 126 disposed on the reservoir-defining structures 120 may be initially in an open position (FIG. 1c) to permit access to the reservoirs for loading the therapeutic agent 116. Once the reservoirs are loaded with therapeutic agent, the covers 126 may be moved into a final position (FIG. 1b). As explained herein above, the softer material of the posts or wires may facilitate deformation. In the final position, an opening 128 may remain to allow the release of the therapeutic agent 116 therethrough in vivo. Further, since the posts or wires are not touching one another, cracking and/or fracturing of the coating during stent expansion may be limited and/or prevented.

As an alternative to having covers 126, the posts or wires may simply have their tops deformed so as to provide a covering over the reservoirs. It will be appreciated that the covering need not completely close the reservoirs, and, in fact, small gaps can facilitate drug elution.

As seen in the examples of FIGS. 1b-d, the reservoir-defining structures 120 are located on the outer surface of the stent strut 117. The reservoir-defining structures 120 may also be located on the inner surface and cut faces of the stent strut 117. In these examples, the reservoir-defining structures 120 form rows of reservoirs 130. As is also seen in these examples, the covers 126 may extend perpendicularly to a longitudinal axis (x) of the stent; however, a multitude of arrangements are possible. For example, the covers may extend parallel to the longitudinal axis of the stent. Likewise, the spacing of the reservoir-defining structures 120 may be varied. For instance, in FIG. 1e, the reservoir-defining structures 120 may be spaced a distance (x), which may be approximately one-hundred microns, apart from each other. In other embodiments, this dimension may change. Indeed, the length, width, and/or height of these reservoir-defining structures 120 may be varied depending upon the application.

As seen in FIG. 1e, each column 122 and cover 126 may be formed integrally of a vertical portion and a slanted portion. Thus, as seen in FIGS. 1b-c, the reservoir-defining structures 120 may be in the form of the vertical portion 124, and the slanted portion may form the cover 126. In FIG. 1b, the cover 126 may at least partially cover the reservoir 130, thus forming micrometer or nanometer sized openings 128. For example, openings 128 of about one-hundred nanometers may be suitable; however, any suitable sized openings 128 may be used. Accordingly, the size of the openings 128 can be used as at least one factor in controlling the elution rate of the therapeutic agent 116 in vivo. Trigger mechanisms that may release the therapeutic agent 116 in vivo include, but are not limited to, temperature (from room to body), vibration, and bodily fluids (e.g., water content, pH, and ions).

It can be appreciated that the reservoir-defining structures 120 such as the columns 122 shown in FIG. 1e may be spaced and the therapeutic agent 116 may be stored between them. Likewise, the reservoir-defining structures may be porous and some therapeutic agent 116 may be stored within the reservoir-defining structures. The selected spacing and porosity of the columns reservoir-defining structures may facilitate the diffusion of therapeutic agent 116 between the reservoirs 130. In addition, while in these examples, the columns 122 are shown having a square cross-section, they may other cross-sections as well, including, but not limited to, circular, s-curved, triangular, and arced cross-sections.

The reservoir-defining structures 120, and columns 122 which comprise the reservoir-defining structures 120, may be formed of ceramics, bio-ceramics, polymers, metals, and combinations of these materials. The reservoir-defining structures 120 and columns 122 may be fabricated using any suitable vapor deposition technique. For example, chemical vapor deposition or physical vapor deposition processes may be used. Chemical vapor deposition processes utilize controlled chemical reactions to deposit films. Physical vapor deposition processes generally involve ejecting atoms from a source material onto a flat surface of a substrate by evaporating the source material or bombarding it with ions. In the examples shown, a physical vapor deposition process utilizing glancing angle deposition (GLAD) may be used.

As described in "An Overview of Thin Films and GLAD," written by Rob Josesph (1996), and published on the University of Alberta's engineering website, the entire contents of which are hereby incorporated by reference, the GLAD process utilizes thermal and electron-beam evaporation to heat a source material until it vaporizes or sublimates and ejects atoms into a chamber. Electron-beam evaporation uses a high beam of high-energy electrons to excite the source material. When incident atoms from the source reach the substrate, the atoms may rearrange themselves into energetically favorable positions. A variety of factors may influence rearrangement of the atoms including, but not limited to, the temperature of the substrate, incident atom energy, and film-substrate molecular interactions. Small nuclei can form on the substrate and may grow until they become large enough to interact with each other. Thus, the nuclei can coalesce and a continuous film can be formed. The deposition may occur in a vacuum chamber to facilitate uniformity.

The GLAD process differs from conventional thin film vapor deposition processes in that it utilizes highly oblique glancing deposition angles. For instance, the glancing angle can include angles greater than 80° (e.g., measured between the normal direction of the substrate and the direction of incident vapor). At these angles, atoms already deposited on the substrate may create atomic shadows behind them, thus shielding that area from the other incident atoms. Further film growth in these regions can be limited and/or prevented. Using the GLAD process, gradations of porosity may be introduced into the film by tilting the substrate away from the deposition source. By restricting where incident atoms can bond to the substrate, the shadowing effect facilitates joining of the incident atoms with nuclei already formed on the surface. As a result, the incident atoms may be more likely to contact the nuclei on the side facing the vapor source. Under glancing angle conditions, these nuclei may continue to grow, such as in a slanted fashion to form a series of slanted columns.

Further, the GLAD process may utilize motors to move the substrate. For example, one motor can change the glancing angle while another motor moves the substrate about a central axis perpendicular to the film surface. Angles of rotation may also be used to change the position of the evaporator source. Further, various speeds can be used throughout the deposition to provide a method of control over the film structure.

As seen in FIG. 1d, in accordance with certain embodiments of the present invention, a guide member 121 may be used with the GLAD process to facilitate utilization of the process with a three dimensional structure such as a stent.

When using the GLAD process to form reservoir defining structures 120 on the surface of a medical device such as a strut 117 of a stent (which may be rotating), it may be difficult to maintain the preferred glancing angles. Therefore, a guide member 121 with a slot(s) 125 may be positioned between the deposition source providing deposition material 123 and strut 117. The slot(s) may be parallel to the stent axis and may prevent deposition material having incorrect glancing angles from reaching the stent surface.

The GLAD process may be used to develop various microstructures, including but not limited to, posts, chevrons, helices, slanted posts, and vertical posts.

The GLAD process may also be used to produce porous coatings of any size including porous coatings on the order of a few nanometers. In addition, it may be possible to build a gradation in porosity in the coating so that the pore size increases or decreases from one side of the microstructure to another.

The GLAD process is discussed in more detail in U.S. Pat. No. 5,866,204 to Robbie et al., filed Jul. 23, 1996, and U.S. Pat. No. 6,206,065 to Robbie et al., filed Jul. 30, 1997, the entire contents of which are hereby incorporated by reference.

In contrast to some conventional thin film deposition techniques, the techniques described in the above-identified patents may utilize highly oblique or glancing deposition angles to form various microstructures. Microstructures which may be formed using the above-identified processes include, but are not limited to, chevrons, helices, slanted columns, vertical columns, and combinations thereof. As discussed in the above-referenced patents, various depositional periods may be used to alter the direction of growth of a particular microstructure and/or to create covers for the microstructures.

In FIG. 1e, it can also be seen that the region forming a joint between the vertical portions and slanted portions may be fatigued (depicted by dashed line). The fatigued section may facilitate movement of the covers 126 between the open (FIG. 1c) and final positions (FIG. 1b).

In alternative arrangements, the reservoir-defining structures 120 or covers 126 may be formed of thermal shape memory alloys which may move depending on temperature. For example, the covers 126 may be pre-shaped during fabrication so that while in room temperature the covers 126 may be in the closed position, the medical device may be, in this example, cooled to a lower temperature, so that cover can be opened to load therapeutic agent. Once the device is positioned in the body, due to an increase in temperature, the covers 126 can move back to the pre-set (closed) position.

Other arrangements may be used for closing the lids in accordance with certain embodiments of the present invention. For example, pressure waves, such as acoustic shockwaves, may be used for closing the lids. In other examples, a crimper system may be used to close the lids. The crimper system may include a mandrel for placing the medical device thereon and an elastic tube for compressing the lids by hydraulic pressure. Still other examples may include an inner C-shaped tube and an outer cylindrical tube which can be pressurized in order to compress the C-clamp to close the lids. The tubes may be elastic.

FIG. 2 shows a portion of an implantable medical device 217 with a plurality of reservoir-defining structures 220 forming reservoirs 230 loaded with therapeutic agent 216 as may be employed with certain embodiments of the present invention. In this illustration, the covers 226 are in the open position to facilitate loading. In FIG. 2, although the covers 226 of the reservoir-defining structures are slanted, the openings 228 formed between each cover 226 and reservoir 230 are greater than the openings 128 of FIG. 1b. Accordingly, when the covers 226 are in the open position, the reservoirs 230 may be easier to load. Suitable techniques for loading the reservoirs 230 include, but are not limited to, dip coating, immersion, and spray coating.

In these systems, the therapeutic agent 216 may be dissolved in a solvent, the therapeutic agent 216 and solvent solution loaded within the reservoirs 230, and the solvent thereafter evaporated using vacuum or pressure.

Any suitable solvent that dissolves a solid, liquid, or gaseous solute to form a solution may be used. For example, various solvents such as dimethylformamide (DMF), tetrahydroforum (THF), and toluene, may be selected depending upon desired viscosities and/or surface tension values of the therapeutic agent 216 and solvent solution. Still further, pressure and temperature may be varied during loading. For instance, the temperature may be varied to achieve desired viscosities and/or surface tensions for the therapeutic agent 216 and solvent solution to facilitate loading.

Figure 3:
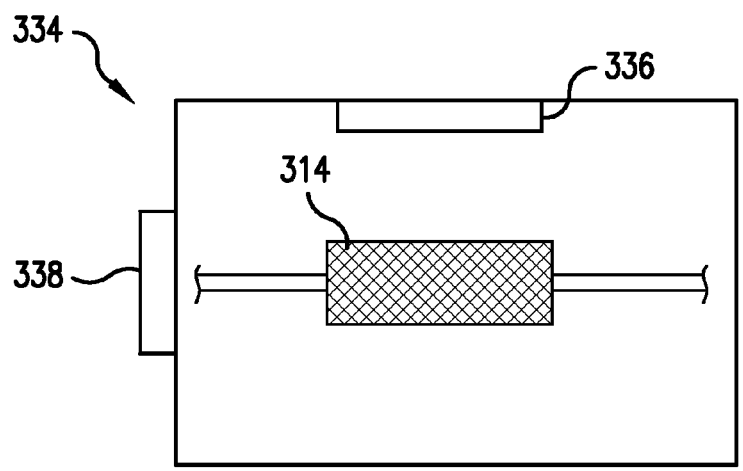
FIG. 3 shows a system for loading implantable medical devices with therapeutic agent as may be employed in accordance with certain embodiments of the present invention.

As seen in FIG. 3, the medical device 314 may be rotatably positioned within a vacuum chamber 334 to load the reservoirs with therapeutic agent. The vacuum chamber 334 may be used for removing air from the reservoirs prior to loading, varying coating parameters, and evaporating solvent from the medical device 314 following loading. In the example, the vacuum chamber 334 can include a spray nozzle 336 in communication with a coating source and a vacuum source 338.

Figure 4:
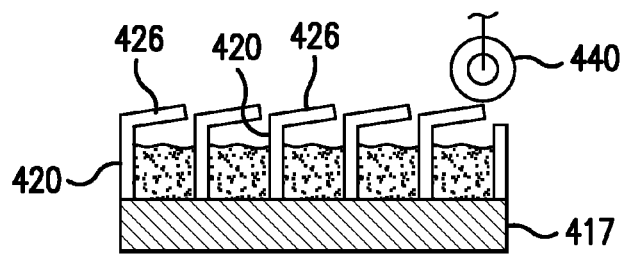
FIG. 4 shows a system for moving a plurality of covers to final positions as may be employed in accordance with certain embodiments of the present invention.

FIG. 4 shows a system for moving the covers 426 from open positions to final positions. In the example, a roller 440 may be used to move the covers 426; however, other suitable techniques may be used. In the example, the roller 440 may be connected to a machine tool (not shown) which can be configured to position the roller 440 in the x, y, and z directions. Likewise, the implantable medical device may be positioned in the x, y, and z directions.

In the examples shown, a bio-compatible layer may be placed on the reservoir-defining structures to promote endothelial re-growth. For example, bio-compatible coatings may facilitate endothelialization of the medical device, such as with the struts of a stent.

FIG. 5 shows a flow chart including method steps that may be employed with certain embodiments of the present invention for making an implantable medical device for releasing a therapeutic agent. Step 510 may include providing an implantable medical device having a medical device body. Step 520 may include positioning a plurality of reservoir-defining structures on a surface of the body to form a plurality of reservoirs. Step 530 can include loading therapeutic agent into the reservoirs. Step 540 may include covering the reservoirs almost completely such that an opening exists so that the therapeutic agent may release when the medical device is implanted.

In embodiments, not shown, the sequence of method steps may be reordered and steps may be added or removed. The steps may also be modified.

Figure 6A:
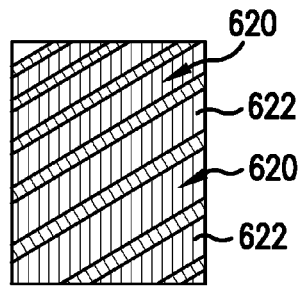
FIGS. 6a-h show alternative reservoir-defining structure arrangements which may be employed in accordance with certain embodiments of the present invention.
Figure 6B:
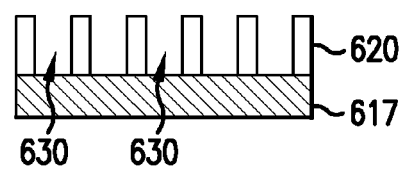

FIGS. 6a-b show an alternative arrangement of reservoir-defining structures 620 for forming reservoirs 630 on surfaces of an implantable medical device 617 and releasing therapeutic agent as may be employed in accordance with certain embodiments of the present invention. In this example, which is similar to that of FIGS. 1a-c, the plurality of reservoirs 630 may also be formed in between a plurality of reservoir-defining structures 620 to store therapeutic agent. In this example, the reservoir-defining structures 620 may be comprised of a plurality of vertical columns 622.

Any suitable fabrication techniques may be used for the reservoir-defining structures 620 and columns 622. For example suitable fabrication techniques may include, but are not limited to, chemical vapor deposition and physical vapor deposition, including the thin film deposition techniques described herein with respect to the previously described arrangement.

As seen in FIGS. 6c-f, the reservoirs 630 may be loaded with a therapeutic agent 616 and solvent solution. The reservoirs 630 may be loaded in accordance with techniques set forth in the previously described arrangement, for example, via immersion. Following loading, a cover(s) 626, such as a cap or coating, can be positioned over the reservoirs 630. In these examples, the cover(s) 626 may extend over the reservoirs 630 entirely.

Figure 6C:
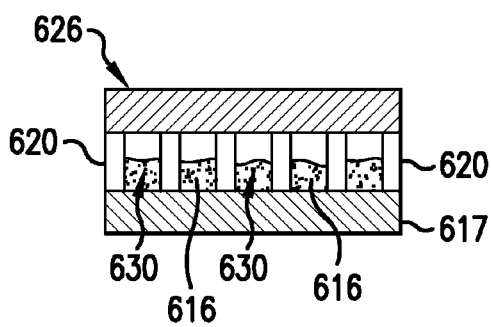
Figure 6D:
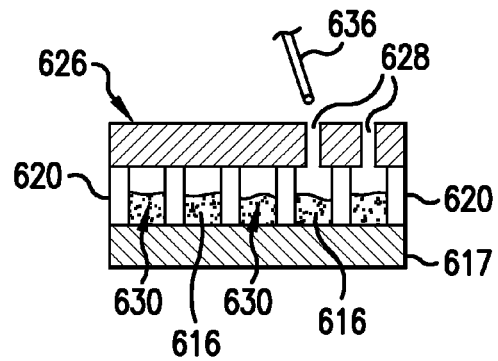

FIGS. 6c-d show a cover 626 which extends over the reservoirs 630. In this example, the cover 626 may be a cap fabricated using techniques previously described for making the reservoir-defining structures 120 and columns 122. The cap may be made of the same and/or different materials than the reservoir-defining structures 620 and columns 622. It is also contemplated by embodiments of the present invention that the cover 626 in this example may be any biocompatible coating.

As best seen in FIG. 6d, portions of the cover 626 may be ablated using laser drilling 636 to drill micrometer and/or nanometer sized openings 628 in the cover 626 to control the elution rate of therapeutic agent 616 from the reservoirs 630 in vivo. Ion bombardment may also be a suitable alternative utilized to create the openings 628. The openings 628 may be any suitable size, for example, openings 628 of about one-hundred nanometers may be used.

Figure 6E:
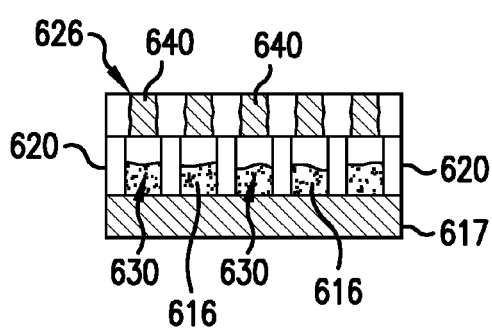
Figure 6F:
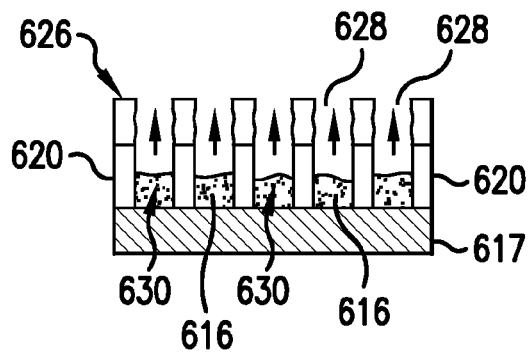

Alternatively, as seen in FIGS. 6e-f, the cover 626 may also be a biocompatible coating comprised at least partially of microporous and/or nanoporous materials 640. For example, portions of the cover 626 may be formed of a biodegradable material such as a magnesium and/or iron alloys and in vivo pores may form in the cover due to the degradation of the biodegradable materials.

Other portions of the cover 626 may be formed of materials that will not erode in vivo (or at least will erode at a slower rate than the biodegradable materials). FIG. 6e shows the cover 626 comprising portions having materials 640 made from magnesium alloy. In FIG. 6f, the device is shown following positioning of the implantable medical device in vivo and erosion of the magnesium alloy material 640. Thus, a plurality of openings 628 may be formed in the cover 626. These openings 628 in the cover 626 may be used to control the release of the therapeutic agent 616 from a respective reservoir 630. The openings 628 may be any suitable size, for example, openings of about one-hundred nanometers may be formed.

As discussed herein, the cover 626 may be a coating. Any suitable coating techniques may be used for applying the coating, including, but not limited to, electrochemical deposition, electroplating, and physical vapor deposition techniques.

Figure 6G:
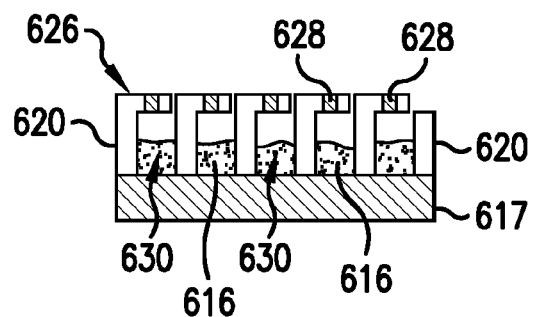

FIG. 6g shows another alternative arrangement for forming reservoirs 630 on a surface of an implantable medical device 617 as may be employed in accordance with certain embodiments of the present invention. In this example, which is similar to that of FIGS. 1a-c, a plurality of reservoirs 630 may be formed between a plurality of reservoir-defining structures 620. Like with the arrangement described in FIGS. 1a-c, covers 626 are moveable between open and final positions; however, in the final position in this example, the covers 626 extend across the reservoirs 640 entirely. In this example, an opening 628 may be formed in each cover 626 by using laser drilling and/or forming portions of each cover 626 of biodegradable portions as previously discussed herein with respect to FIGS. 6c-f. For example, openings 628 may be laser drilled into the covers 626, the reservoirs 630 loaded with therapeutic agent 616, and the covers 626 moved to the final position to cover the reservoirs 630 entirely.

Figure 6H:
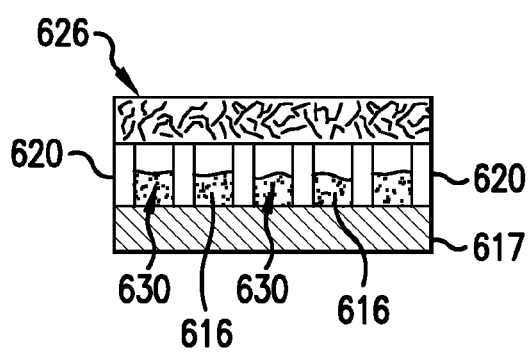

In still other arrangements, as shown in FIG. 6h, the cover 626 may be comprised of a porous coating applied over the reservoir-defining structures 620 and reservoirs 630 using conventional electrochemical deposition, electroplating, and physical vapor deposition techniques. In vivo, therapeutic agent 616 stored in the reservoirs 630 may release through pores in the cover 626.

FIG. 7 shows a flow chart including method steps that may be employed with certain embodiments of the present invention for making a implantable medical device for releasing a therapeutic agent. In the example of FIG. 7, step 710 can include providing a medical device body. Step 720 may include positioning a plurality of reservoir-defining structures on a surface of the body to form a plurality of reservoirs. Step 730 can include loading therapeutic agent into the reservoirs. Step 740 may include covering the reservoirs with a cover. Step 750 may include forming an opening in the cover so that the therapeutic agent may release through the opening when the medical device is implanted.

In embodiments, not shown, the sequence of steps may be reordered and steps may be added or removed. The steps may also be modified.

Figure 8A:
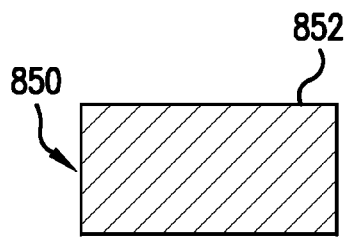
FIG. 8a shows a cross-sectional view of a strut of a stent as may be employed in accordance with certain embodiments of the present invention.
Figure 8B:
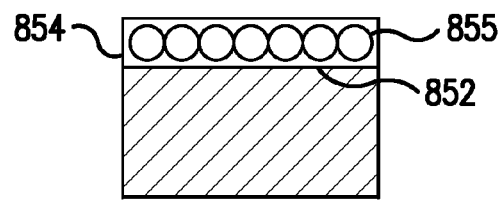
FIGS. 8b-d show the stent strut of FIG. 8a having coating layer(s) located on an outer surface.
Figure 8C:
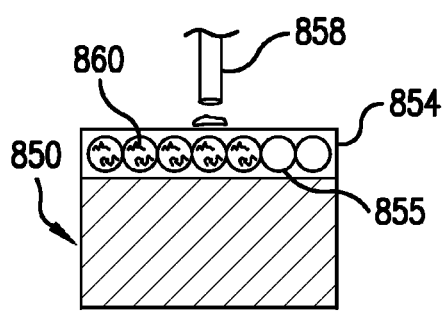
Figure 8D:
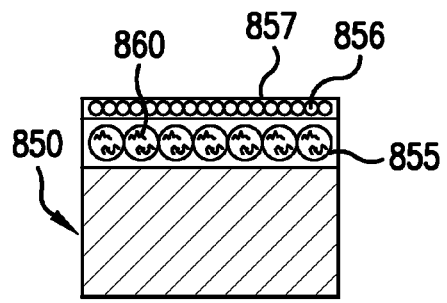

As seen in FIGS. 8a-d, in accordance with some other embodiments, a medical device may be coated with a plurality of porous coating layers such as microporous and/or nanoporous coatings. These coating layers may be polymer-free. In FIG. 8a, a cross-sectional view of a strut 850 of a stent (FIG. 1a) having an outer surface 852 is shown. As seen in FIG. 8b, the outer surface 852 of the strut 850 may be coated with a reservoir layer 854. Turning to FIG. 8d, it can be seen that the outer surface 852 of the strut 850 may also be coated with a membrane layer 856. Although two layers 854, 856 are shown in this example, any number of layers may be used.

In FIG. 8b, the reservoir layer 854 is disposed adjacent to the outer surface 852 of the strut 850. The reservoir layer 854 can comprise a plurality of pores 855. The pores 855 may be any suitable size which facilitates loading of the pores 855 with therapeutic agent 860. For example, pores sizes between 100 nanometers and 1 micrometer may be used.

The reservoir layer 854 may be applied or formed using any suitable process. For instance, chemical and physical vapor deposition processes (e.g., GLAD, ion bombardment, laser etching, irox rice-grain morphology processes, etc.) may be used.

In the example, the reservoir layer 854 is formed in a surface layer of the stent using ion bombardment. The ion bombardment process may utilize ionized gases such as Argon and/or Helium to bombard a surface of a substrate, in this case the stent, to form a porous layer in a surface layer of the substrate. In the example, the ion bombardment process may be used to form a reservoir layer 854 in a top layer of the outer surface 852 of the strut 850; however, other arrangements are possible. For example, the reservoir layer 854 may be formed on inner, outer, and/or cut faces of the struts which comprise the stent.

After the porous reservoir layer 854 is formed, pores 855 of the reservoir layer 854 may be loaded with therapeutic agent 860 using conventional loading techniques including, but not limited to, dip coating, spray coating, and roll coating. In the example, spray nozzle 858 is shown for loading the therapeutic agent 860.

Following loading of the pores 855 with therapeutic agent 860, a membrane layer 856 may be formed or applied over at least portions of the reservoir layer 854. This membrane layer 856 may also be comprised of pores 857. Any suitable pore size may be used for the membrane layer 856. The pore size can facilitate modulation and controlled release of the therapeutic agent in vivo. Further, the average pore size of the pores 857 of the membrane layer 856 may be less than the average pore size of the pores 855 of the reservoir layer 854. For example, pores between 100 nm and 1 nm may be suitable. The larger pores for the reservoir layer facilitate drug loading, while the smaller pores of the membrane layer help control release of the therapeutic agent.

Although the membrane layer 856 may be formed using any suitable process, in the example the GLAD process, described herein above in detail, is used for forming the membrane layer 856. The GLAD process may be used to produce porous coatings of any size including porous coatings on the order of a few nanometers. In addition, using the GLAD process, it may be possible to build a gradation in porosity in the membrane layer 856. For example, in certain examples, the average pore size of the membrane layer 856 may be larger near the reservoir layer 854 side of the membrane layer 856 than the average pore size proximate to the outer surface of the membrane layer 856.

The membrane layer 856 may be made from any biocompatible material. For example, titanium, stainless steel, and other metals or oxides may be used.

FIG. 9 shows a flow chart including method steps that may be employed with certain embodiments of the present invention for making a implantable medical device for releasing a therapeutic agent. In the example of FIG. 9, step 910 may include providing a medical device having inner and outer surfaces. Step 920 may include forming a first porous layer having a first average pore size on at least one of the inner and outer surfaces. Step 930 may include loading therapeutic agent into the first porous layer. Step 940 may include forming a second porous layer with a second average pore size on top of an outer surface of the first porous layer, wherein the second average pore size is less than the first average pore size.

In embodiments, not shown, the sequence of steps may be reordered and steps may be added or removed. The steps may also be modified.

Figure 10A:
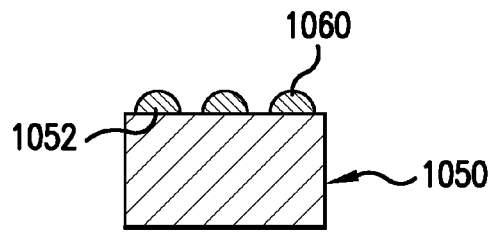
FIG. 10a shows a cross sectional view of a strut of a stent having a plurality of protrusions located on an outer surface as may be employed in accordance with certain embodiments of the present invention.

In still another embodiment, as seen in FIGS. 10*a-e*, a series of protrusions 1060 may be applied or formed onto a surface of a medical device, in this case struts of a stent. In the example, a series of protrusions 1060 can be disposed onto an outer surface 1052 of the strut 1050. As seen in FIG. 10*a*, the protrusions 1060 can be spaced, and in other arrangements, not shown, it is contemplated by embodiments of the present invention that the protrusions 1060 may be connected. In the example, the protrusions 1060 are generally hemispherical; however, any suitable shapes and sizes may be used. Likewise, in the example, the protrusions 1060 are made from polymer; however, any material configured to melt or to be dissolved away may be used. The protrusions 1060 may be applied or formed on the medical device surface by any suitable means which are well known in the art.

Figure 10B:
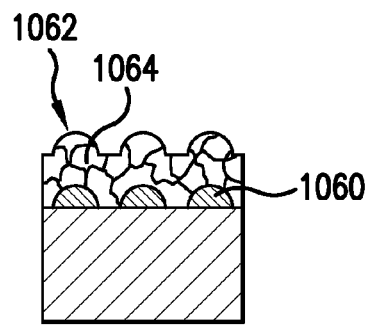
FIGS. 10b-e show the stent strut of FIG. 10a having coating layer(s) located on an outer surface.

Turning to FIG. 10*b*, a membrane layer 1062 comprised of pores 1064 may be formed on top of the protrusions 1060 and the outer surface 1052 of the strut 1050. This membrane layer 1062 may be formed using any process described herein above with respect to the other embodiments. In the example, the GLAD process is used to form the membrane layer 1062. The pores 1064 may be any suitable size, for example, pores sizes between 100 nm and 1 micrometer may be used.

Figure 10C:
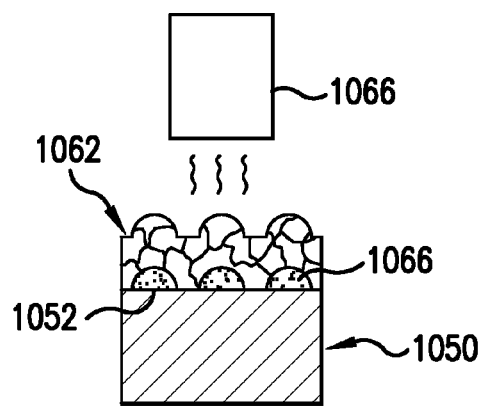

As seen in FIG. 10*c*, once the membrane layer 1062 is formed, thermal energy may be applied to the strut 1050 and/or membrane layer 1062 from a heat source 1066. In addition, suitable processes such as dissolution or plasma heating can be used. The thermal energy applied to the strut 1050 and/or membrane layer 1062 melts the protrusions 1060. As a result, a series of reservoirs 1066 are formed under the membrane layer 1062.

Figure 10D:
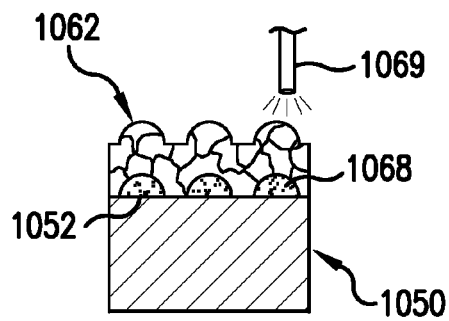

As shown in FIG. 10*d*, the reservoirs 1066 may then be loaded with therapeutic agent 1068 through the membrane layer 1062 via conventional therapeutic agent loading techniques described herein above with respect to other embodiments. In the example, the therapeutic agent 1068 is being sprayed onto the membrane layer 1062 through a nozzle 1069. The therapeutic agent 1068 then travels through the membrane layer 1062 and into the reservoirs 1066.

Figure 10E:
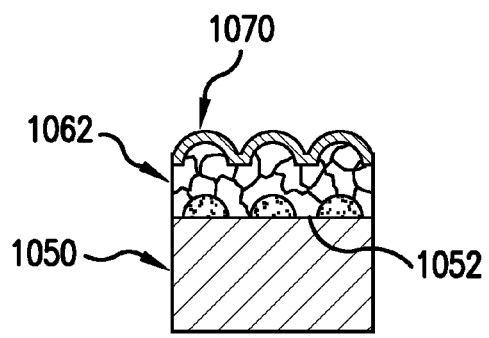

Turning to FIG. 10*e*, once the reservoirs 1066 are loaded, a second membrane layer 1070 comprised of pores may be formed on top of the outer surface of membrane layer 1062.

Any suitable pore size may be used for the second membrane layer 1070 to facilitate the modulation and controlled release of the therapeutic agent 1068 in vivo; however, the average pore size can be less than the pores of membrane layer 1062. For example, pores between 100 nm and 1 nm may be used.

The second membrane layer 1070 may be formed using any suitable process described herein with respect to the other embodiments. In the example shown, the second porous membrane layer 1070 is formed using the GLAD process described in detail hereinabove. As with the other embodiments, the GLAD process may be used to produce porous coatings of any size including porous coatings on the order of a few nanometers.

FIG. 11 shows a flow chart including method steps that may be employed with certain embodiments of the present invention for making a implantable medical device for releasing a therapeutic agent. In the example of FIG. 11, step 1110 may include providing a medical device having inner and outer surfaces. Step 1120 can include applying a series of protrusions to at least one of the inner and outer surfaces. Step 1130 may include forming a first porous layer having a first average pore size on the at least one of the inner and outer surfaces having the protrusions. Step 1140 can include melting the protrusions to form reservoirs under the first porous layer. Step 1150 can include loading therapeutic agent into the reservoirs through the first porous layer. Step 1160 may include forming a second porous layer with a second average pore size on top of an outer surface of the first porous layer, wherein the second average pore size may be less than the first average pore size.

In embodiments, not shown, the sequence of steps may be reordered and steps may be added or removed. The steps may also be modified.

In still yet another embodiment, as seen in FIGS. 12*a-d*, a reservoir layer 1254 may be formed in a surface of the medical device 1214 using, for example, ion bombardment or a laser. In the case of a laser, as shown, a laser 1272 may be used having short pulse durations of radiation. The laser 1272 may be used to create pores in or roughen a thin surface layer of the medical device 1214 without substantially heating the rest of the medical device.

Figure 12A:
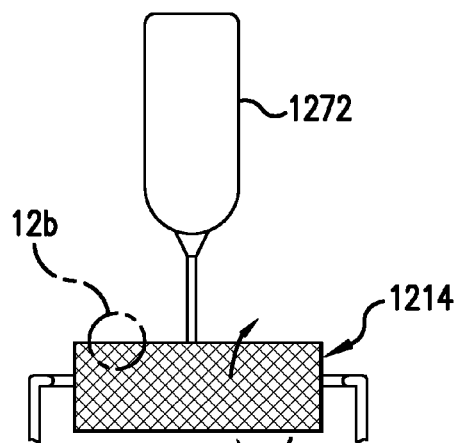
FIG. 12a shows a laser forming a reservoir layer in a stent as may be employed in accordance with embodiments of the present invention.
Figure 12B:
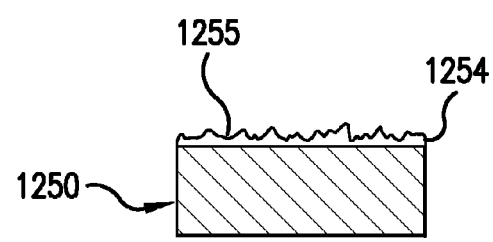
FIG. 12b shows a cross-sectional view taken along line 12b-12b in FIG. 12a showing an enlarged view of a portion of the reservoir layer.

For example, as seen in FIGS. 12*a-b*, a laser 1272 may be used to create pores in or roughen surfaces of a stent strut 1250. An inner surface, outer surface, and cut faces of the stent strut 1250 may be made porous or roughened. A plurality of pores 1255 can be formed between the peaks and valleys of the roughened surface. The porous or roughened surface may promote adhesion of a coating layer formed on the stent strut 1250. The pores 1255 formed may be micrometer and/or nanometer size pores. The laser 1272 may be used to selectively form localized reservoirs on a surface of a stent. For example, pores having a first porosity may be formed on an outer surface of a first area of the stent, while pores having a second porosity may be formed on an outer surface of a second area of the stent.

In other embodiments, surfaces of a stent strut 1250 may be made porous or roughened using the laser 1272 in order to promote endothelial cell adhesion and migration. In addition, other embodiments may include creating pores in or roughening a layer formed on a surface of the stent strut using laser 1272 to promote the adhesion of a successive layer. Still other embodiments can include creating pores in or roughening a stent strut 1250 surface using laser 1272 to enhance crimped stent adhesion to a balloon, such as to prevent embolisms.

Suitable lasers may include excimer and femto type lasers. An excimer laser may use pulse durations of less than about two nanoseconds ($10^{-9}$) seconds. Alternatively, a femto laser may use pulse durations of less than about one hundred femtoseconds ($10^{-15}$) seconds. The lasers may be used to rapidly melt a very thin surface layer of the medical device. This surface layer then solidifies to cause the roughened surface forming pores.

Figure 12C:
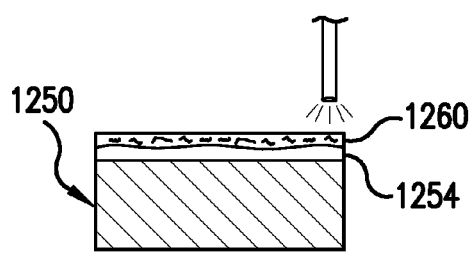
FIG. 12c shows the reservoir layer of FIG. 12b being loaded with therapeutic agent.

As seen in FIG. 12c, therapeutic agent 1260 may then be loaded within the pores 1255 of the reservoir layer 1254.

Figure 12D:
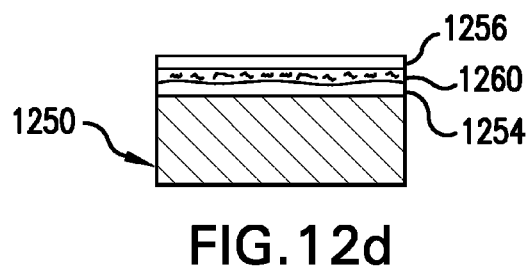
FIG. 12d shows a membrane layer being applied to an outer surface of the reservoir layer of FIG. 12c.

As seen in FIG. 12d, the reservoir layer 1254, which is loaded with therapeutic agent 1260, can then be coated with a porous membrane layer 1256 to regulate and modulate the elution of therapeutic agent from the reservoir layer in vivo. In the example, a continuous porous membrane 1256 layer is shown; however, the membrane layer may be discontinuous. Further, the pore size of the membrane layer 1256 may be varied from one area of the stent to another (e.g., inner diameter v. outer diameter and/or end v. center) to modulate the release profile from different surfaces).

The membrane layer 1256 can be formed of an inorganic material, and may be applied using any suitable process including, but not limited to, the GLAD process, accelerated nanoparticle deposition, chemical vapor deposition, physical vapor deposition, or pulsed laser deposition. The roughened surface of the reservoir layer 1254 can facilitate adherence and/or anchoring of the membrane layer 1256.

The GLAD deposition may be conducted at temperatures around 100° C. and hence active agents/polymers which can withstand that temperature may be pre-loaded. For active agents that cannot withstand 100C, post-loading techniques may be used. In addition, certain embodiments of the present invention may include depositing durable metallic or oxide cap layers over polymeric substrates using GLAD combined with High Power Pulsed Magnetron Sputtering (HPPMS). The surface energy of a polymer substrate can be low. Thus, the metallic or oxide coating may be easily delaminated and it may be difficult to create a metallic or oxide layer on a polymeric substrate using conventional coating methods. Therefore, GLAD-HPPMS can generate highly durable nanoporous cap layers. HPPMS deposition may assist with adhering the coating materials while the GLAD process generates nanoporous morphology in the cap layer.

This GLAD and/or GLAD-HPMMS processes may address drawbacks that can arise using conventional coating methods such as dip coating, PVD, or CVD. For example, using these conventional methods, since the nanoporous coating will be deposited inside of the pores of the reservoir layer, it may not retain the volume of the pores for drug loading.

In other embodiments, the peaks and valleys of the reservoir layer 1254 may be flattened or smoothed. This flattening or smoothing step may slow the elution of the therapeutic agent 1260 in vivo.

FIG. 13 shows a flow chart including method steps that may be employed with certain embodiments of the present invention for making a implantable medical device for releasing therapeutic agent. In the example of FIG. 13, step 1310 may include providing a medical device having inner and outer surfaces. Step 1320 can include forming a reservoir layer comprised of a plurality of pores in or on at least one of the inner and outer surfaces, as by a laser or ion bombardment. Step 1330 may include loading the plurality of pores with therapeutic agent. Step 1340 can include forming a membrane layer on top of an outer surface of the reservoir layer.

In embodiments, not shown, the sequence of steps may be reordered and steps may be added or removed. The steps may also be modified.

While various embodiments have been described, other embodiments are possible. It should be understood that the foregoing descriptions of various examples of the implantable medical devices having reservoirs and methods for making and loading the same are not intended to be limiting, and any number of modifications, combinations, and alternatives of the examples may be employed to facilitate the effectiveness of delivering therapeutic agent from the reservoirs to a target site of a patient.

The term "therapeutic agent" as used herein includes one or more "therapeutic agents" or "drugs." The terms "therapeutic agents" or "drugs" can be used interchangeably herein and include pharmaceutically active compounds, nucleic acids with and without carrier vectors such as lipids, compacting agents (such as histones), viruses (such as adenovirus, adenoassociated virus, retrovirus, lentivirus and α-virus), polymers, hyaluronic acid, proteins, cells and the like, with or without targeting sequences.

Specific examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; anti-proliferative agents such as enoxaprin, everolimus, zotarolimus, angiopeptin, rapamycin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vasoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the insertion site. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMPs"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMPs are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNAs encoding them.

The examples described herein are merely illustrative, as numerous other embodiments may be implemented without departing from the spirit and scope of the exemplary embodiments of the present invention. Moreover, while certain features of the invention may be shown on only certain embodiments or configurations, these features may be exchanged, added, and removed from and between the various embodiments or configurations while remaining within the scope of the invention. Likewise, methods described and disclosed may also be performed in various sequences, with some or all of the disclosed steps being performed in a different order than described while still remaining within the spirit and scope of the present invention.

What is claimed is:

1. A method for making an implantable medical device for releasing therapeutic agent, comprising:
   providing a medical device body;
   positioning a plurality of reservoir-defining structures on a surface of the body to form at least one reservoir defined by the reservoir-defining structures;
   loading therapeutic agent into the reservoir; and
   moving a portion of at least one of the plurality of reservoir-defining structures from a first position to a second position so as to cover the reservoir almost completely such that an opening exists for the reservoir so that the therapeutic agent is released when the medical device is implanted,
   wherein the portion of the at least one of the plurality of reservoir-defining structures is moved after the therapeutic agent is loaded.

2. The method of claim 1, wherein the reservoir-defining structures comprise a plurality of columns extending upwardly from the surface of the body, the columns forming walls of the reservoirs.

3. The method of claim 2, wherein the surface of the body forms a bottom surface for each reservoir.

4. The method of claim 2 wherein the reservoir-defining structures comprise a plurality of dividers formed by the columns.

5. The method of claim 2 wherein the reservoir-defining structures comprise a plurality of plates formed by the columns.

6. The method of claim 1 wherein the opening is between about one and one-hundred nanometers.

7. The method of claim 1 wherein the portion is a thermal shape memory alloy.

8. The method of claim 1, wherein the portion is a slanted portion.

9. The method of claim 8, wherein a region of the reservoir-defining structures is fatigued so as to facilitate movement of the slanted portion to the second position.

10. The method of claim 1, wherein the first position is an open position, and the second position is a final position, and
   wherein when the portion is moved from the first to the second position, the portion is moved closer to the reservoir.

11. The method of claim 1, wherein the reservoir-defining structures are applied using a GLAD process.

12. The method of claim 1, wherein the medical device body is a stent.

13. A method for making an implantable medical device for releasing therapeutic agent, comprising:
providing a medical device body;
positioning a plurality of reservoir-defining structures on a surface of the body to form at least one reservoir defined by the reservoir-defining structures;
loading therapeutic agent into the reservoir;
covering the reservoir with a cover; and
forming a hole in the cover ex vivo so that the therapeutic agent releases through the opening when the medical device is implanted.

14. The method of claim 13 wherein the hole is centrally disposed.

15. The method of claim 13 wherein the hole is between about one and one-hundred nanometers.

16. The method of claim 13 wherein the cover is made from the same material as the plurality of reservoir-defining structures.

17. The method of claim 13 wherein the cover is applied using a GLAD process.

18. The method of claim 13 wherein the cover is comprised of a biocompatible coating.

19. The method of claim 13, wherein the reservoir-defining structures comprise a plurality of columns extending upwardly from the surface of the body, the columns forming walls of the reservoirs.

20. The method of claim 19, wherein the surface of the body forms a bottom surface for each reservoir.

21. The method of claim 13, wherein the reservoir-defining structures are applied using a GLAD process.

22. The method of claim 13, wherein the medical device body is a stent.

23. The method of claim 13, wherein the hole is formed by laser drilling.

* * * * *